United States Patent [19]

Dolfini et al.

[11] 4,071,682

[45] Jan. 31, 1978

[54] 7-α SUBSTITUTED IMINO 7-β SUBSTITUTED THIO CEPHALOSPORIN DERIVATIVES

[75] Inventors: Joseph Edward Dolfini, Princeton; William A. Slusarchyk, Belle Mead; William Henry Koster, Pennington, all of N.J.

[73] Assignee: E. R. Squibb & Sons, Inc., Princeton, N.J.

[21] Appl. No.: 668,007

[22] Filed: Mar. 18, 1976

Related U.S. Application Data

[62] Division of Ser. No. 395,201, Sept. 7, 1973, abandoned.

[51] Int. Cl.$^2$ ............................................ C07D 501/18
[52] U.S. Cl. ...................................................... 544/21
[58] Field of Search .................................... 260/243 C

[56] References Cited

U.S. PATENT DOCUMENTS

| | | | |
|---|---|---|---|
| 3,840,533 | 10/1974 | Dolfini et al. | 260/243 C |
| 3,875,146 | 4/1975 | Christensen et al. | 260/243 C |
| 3,947,413 | 3/1976 | Christensen et al. | 260/243 C |
| 3,954,731 | 5/1976 | Spitzer | 260/243 C |
| 3,954,744 | 5/1976 | Dolfini et al. | 260/243 C |

OTHER PUBLICATIONS

March, Advanced Organic Chemistry, p. 301, 1968.

*Primary Examiner*—Nicholas S. Rizzo
*Assistant Examiner*—David E. Wheeler
*Attorney, Agent, or Firm*—Lawrence S. Levinson; Merle J. Smith

[57] ABSTRACT

An improved, versatile method for producing 7-cephalosporin derivatives having a 7-alkylthio or 7-arylthio group which comprises treating a 7-substituted imino halide, imino ether or iminothio ether of 7-aminocephalosporanic acid, 7-amino-3-desacetoxycephalosporanic acid and the like with a thiolating agent in the presence of a base, to obtain the thio derivative. These products are particularly useful for conversion to 7α-alkylthio or 7α-arylthio-7-acylamino intermediates which are converted to lower alkoxy cephalosporin derivatives useful as antibacterial agents.

9 Claims, No Drawings

7-α SUBSTITUTED IMINO 7-β SUBSTITUTED THIO CEPHALOSPORIN DERIVATIVES

This is a division of application Ser. No. 395,201, filed Sept. 7, 1973 now abandoned.

BACKGROUND OF THE INVENTION

A variety of 7α-lower alkoxycephalosporins of the general formula

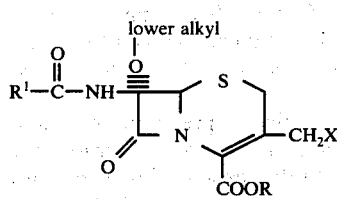

especially those wherein the lower alkoxy group is methoxy, have been disclosed to be useful antibacterial agents. See, for example, Belgian Pat. No. 768,528 and Netherlands patent publication No. 72.04982. Valuable intermediates for the production of these products are those cephalosporins wherein there is a sulfur group in the 7-position, a radical which is replaceable by the alkoxy group. It is an object of this invention to provide an improved process for synthesizing such products by means of novel intermediates.

SUMMARY OF THE INVENTION

This invention relates to an improved, flexible method of synthesizing valuable intermediates for the production of 7α-lower alkoxy, especially 7α-methoxy, derivatives of 7-aminocephalosporanic acid and related compounds.

It has been found, according to the process of this invention, that by using an imino chloride, imino ether or imino thioether derivative of a 7-aminocephalosporanic acid as the starting material, an alkylthio or arylthio group can be readily introduced into the 7-position. These thiolated intermediates can be converted to 7α-alkylthio or 7α-arylthio-7-acylaminocephalosporanic acid derivatives which in turn can be converted to the desired 7-alkoxycephalosporins.

The method of this invention comprises treating a 7-substituted imino halide, 7-substituted imino thioether or 7-substituted imino ether of 7-aminocephalosporanic acid, or the like, with an alkyl or aryl thiolating agent in the presence of a base to introduce the alkylthio or arylthio group into the 7-position. The 7α-alkyl- or 7α-arylthio-7-substituted imino halide intermediate thus obtained is hydrolyzed to a 7α-alkylthio- or 7α-arylthio-7-acyl cephalosporin or, if the moiety desired in the acyl side chain of the final product is not already in place, the imino halide is converted to the corresponding imino ether or imino thioether. Any of these 7α-alkylthio- or 7-arylthio-7-substituted imino ether intermediates or 7α-alkylthio- or 7α-arylthio-7-substituted imino thioether intermediates can be acylated to yield 7-thiolated-7-acylamino cephalosporanic acid derivative. These last compounds are then converted to the desired alkoxycephalosporins [for example by the method of Slusarchyk et al., J. Org. Chem. 38, 943 (1973)] which are useful antibacterial agents.

DETAILED DESCRIPTION OF THE INVENTION

The new method of this invention is a process for producing new intermediates leading to 7-acylaminocephalosporanic compounds of the formula

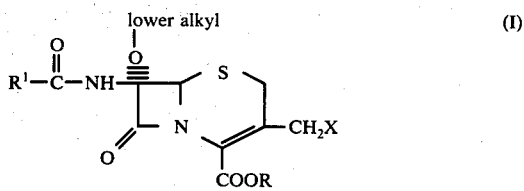

especially wherein the lower alkyl group is methyl.

A variety of cephalosporin compounds characterized by a lower alkoxy group, especially methoxy, in the 7-position have been shown to be useful antibacterial agents. In such compounds, the $R^1$ radical completing the acyl side chain can be any of a wide variety of organic groups. The same obtains with respect to the substituents R and X. See, for example, U.S. Pat. Nos. 3,665,003, 3,668,203, 3,687,949, 3,708,479 and 3,516,997.

Thus it will be seen from the cited sources that such compounds include those wherein $R^1$ represents a variety of organic radicals forming an acyl group with the carbonyl in such cephalosporin compounds. These include lower alkyl groups like methyl, ethyl, propyl and the like, benzyl, phenoxymethyl, α-aminobenzyl, α-carboxylbenzyl, α-aminocyclohexadienylmethyl, thienylmethyl, furylmethyl, pyridylmethyl, cyanomethyl, cyanomethylthiomethyl, α-ureidothienylacetyl, pyridylthiomethyl and many others as shown in said cited material.

R represents such substituents as hydrogen, a salt forming ion including alkali metal, like sodium or potassium, alkaline earth metal like calcium, organic amine radical, e.g., alkylamine especially lower alkylamine like triethylamine, an ester residue like lower alkyl or lower alkanoyloxy-lower alkyl, e.g., methyl, ethyl, pivaloyloxymethyl or the like, and a variety of organic radicals known for this purpose.

X, too, represents a variety of known radicals in compounds of this kind, for example, hydrogen, lower alkanoyloxy like acetoxy, lower alkylthio like methylthio, lower alkoxy like methoxy, carbamoyloxy, 2-methyl-1,3,4-thiadiazol-5-ylthio, etc.

The invention thus relates to a new process for producing a broad group of cephalosporin derivatives of formula I wherein R, $R^1$ and X are substituents known in this art.

The process of this invention provides a flexible, versatile means for producing products of this description.

The process of this invention utilizes as starting material an imino halide, imino ether or imino thioether of a 7-aminocephalosporanic acid having the formula

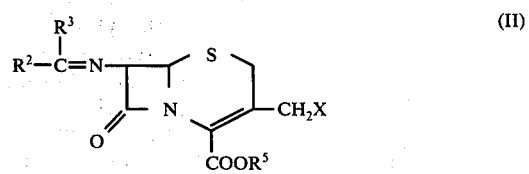

When II represents an imino halide, $R^3$ is chlorine or bromine and $R^2$ is an aryl group, aralkyl, lower alkyl or substituted lower alkyl group, e.g., methyl, methoxymethyl, methylthiomethyl, cyanomethyl, cyanomethylthiomethyl, phenylthiomethyl, phenoxymethyl, benzyl or thienylmethyl. The aryl groups as used throughout refer to phenyl and substituted phenyl radicals wherein the phenyl substituent includes one to three halogens, preferably chlorine or bromine, lower alkyl, nitro or carbo-lower alkoxy, e.g., o-nitrophenyl, p-nitrophenyl, o,p-dichlorophenyl, p-bromophenyl, p-carbomethoxyphenyl. The lower alkyl groups are those containing up to seven carbons, preferably one to four and especially one.

At this stage, in the most effective form of the invention, the carboxylic acid substituent is a more limited version of R forming a protective ester group which is not affected by the reaction step, i.e. t-butyl, nitrobenzyl, methoxybenzyl, trichloroethyl, benzhydryl, trimethylsilyl, acetoxymethyl or pivaloyloxymethyl and these groups are represented by the symbol $R^5$.

When II represens an imino ether. $R^3$ is lower alkoxy, e.g., methoxy, which is preferred, ethoxy, propoxy, isopropoxy, butoxy, etc. or aryloxy, e.g., phenoxy and $R^2$ is hydrogen or lower alkyl as just defined, or an aryl or substituted alkyl group as defined for imino halides. When II represents an imino thioether, $R^3$ is lower alkylthio, e.g., methylthio, ethylthio, propylthio, arylthio, e.g., phenylthio, etc., and $R^2$ is hydrogen, aryl or lower alkyl or substituted lower alkyl as defined for imino halides. $R^5$ is the same as above.

$R^2$ and X in the imino halides, imino ethers and imino thioethers are generally those groups desired in the final product or are readily replaced by those desired in the final product and are of the character described.

The imino halide, imino ether or imino thioether or formula II is made to react with an alkyl or aryl thiolating agent in the presence of a strong base, preferably an organic base, at a reduced temperature, e.g., in the range of about −80° to +10° C. to introduce the 7α-alkylthio or 7α-arylthio group in the 7-position resulting in an intermediate of the formula

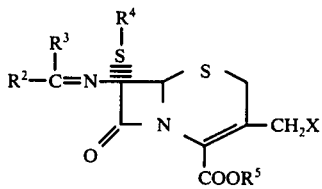

(III)

wherein $R^4$ is lower alkyl, phenyl, benzyl or the latter two with a simple substituent on the phenyl ring, e.g., nitro, halo, especially chloro, bromo, lower alkyl, especially methyl, carbo-lower alkoxy, e.g., carbomethoxy or the like. These include, for example, methyl, ethyl, phenyl, benzyl, p-nitrophenyl, $R^5$, $R^2$, $R^3$ and X are as already defined.

The alkyl or aryl thiolating compound can be one of various thio compounds including lower alkyl sulfenyl halides, e.g., methylsulfenyl chloride and ethylsulfenyl bromide, aryl sulfenyl halides, e.g., phenylsulfenyl chloride; sulfonic acid thio ester derivatives, i.e., lower alkylthio-lower alkylsulfonate or lower alkylthio-arylsulfonates like methylthio mesylate, methylthio tosylate, ethylthio tosylate; lower alkyl- and aryl disulfides, e.g., dimethyl disulfide, diethyl disulfide, diphenyl disulfide, lower alkoxy carbonyllower disulfides, e.g., methoxycarbonyl methyl disulfide, ethoxycarbonyl ethyl disulfide.

The base used in conjunction with the alkyl or aryl thiolating compound can be of a variety of bases including alkali metal-lower alkoxides such as sodium methoxide, lithium methoxide, potassium t-butoxide and the like, alkali metal salts of a secondary amine, e.g., a potassium, sodium or lithium salt of a lower alkylamine, for example, lithium or sodium diisopropylamide, lithium cyclohexylisopropylamide and the like, alkali metal arylalkyl, aryls, and alkyls like triphenyl methyl sodium, triphenylmethyl lithium, phenyl lithium or t-butyl lithium and the like, or alkali metal hydrides like sodium hydride.

This thiolating reaction is preferably effected in an inert atmosphere, such as nitrogen or argon in an organic solvent inert to the reactants involved, for example dioxane, acetonitrile, tetrahydrofuran, dimethylformamide, dimethoxyethane, benzene and the like. The reaction is effected at a reduced remperature, e.g., within the range of about −80° to 0° C., and occurs within a period ranging from several minutes up to about 1 hour.

The thiolating agent is preferably used in a proportion of about one to two equivalents in relation to the starting material of formula II. About one to two equivalents of the base described above also should be present.

The product of the first step of the process is the intermediate of formula III.

The second step of the process comprises conversion of this intermediate of formula III to the desired compound of the formula

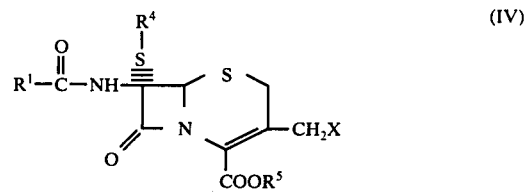

(IV)

either by selective hydrolysis or by acylation, and this is a feature which provides flexibility to the process.

When the imino halide is the starting material, i.e., $R^3$ is one of the halogens in formula III, hydrolysis of this imino halide form, yields a product having the same $R^2$ group as the starting material. This is frequently the preferred modification since the imino halide intermediates usually are obtained in good yield and are readily isolated and purified.

However, when the $R^1$ group desired in the product of formula IV and in the final 7-alkoxy product of formula I is one which is a reactive group under the conditions of reaction or which interferes with the principal reaction, e.g., the formation of the imino halide by a halogenation reaction using a phosphorus halide, or with the thiolation step, or which gives a product not easily separated or worked up, the imino ether or imino thioether (i.e., $R^3$ in formula III is lower alkoxy or lower alkylthio) then becomes the starting material of choice. Such occasions arise, for example, when the $R^1$ group desired in the final product includes a reactive group such as a free amino group, e.g., $R^1$ is α-aminobenzyl, p-hydroxyphenylmethyl or the like, or the reactivity of such groups, without protection, interferes with the formation of the imino halide.

The selective hydrolysis of the imino halide of formula III is accomplished by treating III with one equivalent or less of an organic or inorganic acid catalyst, e.g., a mineral acid like hydrochloric acid or an arylsulfonic acid like p-toluenesulfonic acid, and at least one equivalent of water, for example, an aqueous acid solution of about 0.01N to 5N concentration in a reaction medium like dichloromethane, chloroform, carbon tetrachloride, ethyl acetate, tetrahydrofuran, dimethoxyethane, 1,2-dichloroethane, and the like, preferably at a temperature range of about −30° to +30° C., for a period of about 1 hour to 2 days.

In addition the imino halide of formula III containing the 7-thio group, instead of being hydrolyzed as described above can also be converted to an imino ether or imino thioether of formula III (in which $R^3$ is other than halogen) and then converted to a compound of formula IV by acylation with acyl halide, acid anhydride, mixed anhydride or derivatives thereof, as described below. This alternative is one of the effective variations giving wide flexibility to the process.

The imino halide of formula III is converted to an imino ether of formula III by reacting the imino halide with at least one equivalent of lower alkanol or aryl alcohol, e.g., methanol, ethanol, propanol, in the presence of an organic base like pyridine, N,N-dimethylaniline, or quinoline, preferably one equivalent, in an inert solvent, like acetone, tetrahydrofuran, dioxane, dimethylsulfoxide, dimethylformamide, dimethylacetamide, acetonitrile, dichloromethane, chloroform, 1,2-dichloro ethane, at about a temperature of −30° to +30° C. for a period of about ½ hour to 24 hour depending upon the temperature. The lower alkanols can also be used as the reaction medium in place of the inert solvents mentioned. By substituting for the lower alkanol, a lower alkylthiol such as methyl mercaptan, ethyl mercaptan, propyl mercaptan, etc., an imino thioether of formula III can be prepared.

Acylation of the imino ether or imino thioether of formula III by means of an acyl halide or acid anhydride having the $R^1$ group desired in the final product, i.e., a compound of the formula $R^1COY$ or $(R^1CO)_2O$ wherein $R^1$ has the meaning previously described and Y is halogen, preferably chlorine or bromine, or a mixed anhydride, results in the replacement of the $R^2$ group utilized up to this point in the synthesis with the $R^1$ group desired in the final product. The acylation reaction is accomplished by bringing together the compound of formula III with the acylating agent in a proportion of about one part of the former to about one to two parts of the latter in an organic reaction medium like dichloromethane, chloroform, carbon tetrachloride, 1,2-dichloroethane, benzene, dioxane, dimethoxyethane or ethyl acetate in the presence of at least one equivalent of water or lower alkanol, such as methyl alcohol or ethyl alcohol, and in the presence of one equivalent or less of an organic base, e.g., pyridine or triethylamine, or strong acid, e.g., hydrochloric acid or p-toluenesulfonic acid, at a temperature within the range of about −30° to 50° C., preferably about −10° to +5° C., for a period of about 1 hour to 2 days.

The imino halides, imino ethers and imino thioethers of formula II can be prepared by published methods.

Alternatively, the imino ethers and imino thioethers of formula II can be prepared from ortho esters and ortho thioesters, respectively, by reacting an ortho ester of formula V or orthothio ester of formula V with a 7-aminocephalosporanic acid derivative of formula VI:

wherein $R^3$ is lower alkoxy, lower alkylthio, aryloxy or arylthio,

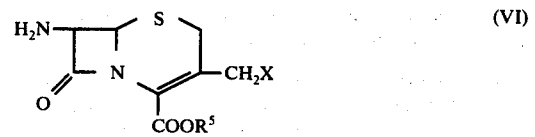

$R^2$, $R^3$ and $R^5$ in formulas V and VI are as previously defined. X represents a variety of known radicals of this kind, for example, hydrogen, lower alkanoyloxy like acetoxy, lower alkylthio like methylthio, lower alkoxy like methoxy, carbamoyloxy, 2-methyl-1,3,4-thiadiazol-5-ylthio, etc. The preparation of the desired imino ether or imino thioethers, by this method, is accomplished by reacting at least one equivalent of the imino ether or imino thioether with one equivalent of 7-aminocephalosporanic acid derivative of formula VI in an inert solvent such as benzene, toluene, xylene, dimethoxyethane, dimethylformamide, dimethylacetamide, dimethylsulfoxide, acetonitrile, etc., at a temperature in the range 0° to 140° C. for a period of about 1 hour to 48 hours depending upon the temperature and solvent. Preferably a catalytic (trace) amount of acid catalyst like p-toluenesulfonic acid, hydrochloric acid, sulfuric acid or the like is present.

The following examples are illustrative of the invention. Temperatures are all on the centigrade scale.

EXAMPLE 1

7-[(Chlorophenylmethylene)amino]desacetoxy cephalosporanic acid t-butyl ester

A mixture of 11.2 g. (30 mmoles) of 7-(benzamido)-desacetoxycephalosporanic acid t-butyl ester, 5.40 g. (44 mmoles) of N,N-dimethylaniline and 9.05 g. (44 mmoles) of phosphorus pentachloride in 100 ml. of dry dichloromethane is stirred at −30° for 1.5 hours under nitrogen. The mixture is poured into ice water, and the organic layer is washed with dilute hydrochloric acid and then water. It is dried ($Na_2SO_4$) and evaporated in vacuo to a residue that is taken up in benzene. The benzene solution is washed four times with dilute hydrochloric acid, dried ($Na_2SO_4$), decolorized with charcoal, and evaporated to a yellow residue. Treatment of the residue with n-hexane and ethyl ether yields 7.47 g. of crystalline product, 7-[(chlorophenylmethylene)amino]desacetoxycephalosporanic acid t-butyl ester, m. p. about 110°–115°, pmr ($DCCl_3$) τ8.45 (9H, s,t-butyl), 7.90 (3H, s, C-3 methyl), 6.63 (2H, q, J=19Hz, C-2), 4.88 (1H, d, J=5Hz, C-6), 4.25 (1H, d, J=5Hz, C-7), 1.7–2.8 (5H, m, aromatics); ir ($CHCl_3$) 1780 (β-lactam C=O), 1715 (ester C=O), and 1645 $cm^{-1}$ (C=N).

EXAMPLE 2

7-[(Bromophenylmethylene)amino]desacetoxycephalosporanic acid t-butyl ester

A mixture of 6 mmoles of 7-(benzamido)desacetoxycephalosporanic acid t-butyl ester, 6 mmoles of N,N-dimethylaniline and 2 mmoles of phosphorous tribromide in 50 ml. of dry dichloromethane is stirred at 0° for 2 hours under nitrogen and poured into ice water. The organic layer is washed with dilute hydrochloric acid, then water, dried ($Na_2SO_4$), decolorized with charcoal, and evaporated in vacuo to obtain the above named product as an amorphous residue.

EXAMPLE 3

7-[(1-Chloro-2-phenylethylidene)amino]desacetoxycephalosporanic acid t-butyl ester A mixture of 1 mmole of 7-(phenylacetamido)-desacetoxycephalosporanic acid t-butyl ester, 1 mmole of phosphorus pentachloride, and 1 mmole of pyridine in 10 ml. of dry dichloromethane is stirred at ambient temperature under nitrogen for 1 hour. The solvent is removed under reduced pressure, and dry benzene is added. The benzene is removed under reduced pressure and additional benzene is added and again removed under vacuum. The addition and removal of benzene is performed at least four times. Benzene is added again, and the benzene solution is clarified by centrifuging in an inert atmosphere. The supernatant is evaporated under reduced pressure yielding 320 mg. of powdery residue containing the above named product. The crude product is sufficiently pure for further transformations. The product has: pmr ($DCCl_3$), $\tau$ 8.47 (9H, s, t-butyl), 7.93 (3H, s, C-3 methyl), 6.03 (2H, s, $-CH_2-C(Cl)=\lambda$ N$-$), 5.00 (1H, d, J=4Hz, C-6), 4.53 (1H, d, J=4Hz, C-7), 2.4–2.8 (5H, broad singlet, aromatics).

EXAMPLE 4

7-[(Chlorophenylmethylene)amino]cephalosporanic acid t-butyl ester

By following the procedure in Example 1 but substituting 7-(phenylacetamido)cephalosporanic acid t-butyl ester for 7-(benzamido)desacetoxycephalosporanic acid t-butyl ester, the above named product is obtained as an amorphous residue.

EXAMPLE 5

7-[[1-chloro-2-(2-thienyl)ethylidene]amino]cephalosporanic acid trichloroethyl ester By following the procedure in Example 3, but substituting 7-(thienylacetamido)cephalosporanic acid trichloroethyl ester for the 7-(phenylacetamido) desacetoxy cephalosporanic acid t-butyl ester, the above named product is obtained as an amorphous residue.

EXAMPLE 6

7-[[1-chloro-2-(cyanomethylthio)ethylidene]amino]-cephalosporanic acid benzhydryl ester By following the procedure in Example 3, but substituting 7-[(cyanomethylthio)acetamido]cephalosporanic acid benzhydryl ester for the 7-(phenylacetamido)-desacetoxycephalosporanic acid t-butyl ester, the above named product is obtained as an amorphous residue.

EXAMPLE 7

7-[Methoxyphenylmethylene)amino]desacetoxycephalosporanic acid t-butyl ester

A mixture of 393 mg. (1 mmole) of the imino chloride product from Example 1, 90 ml. (1.1 mmole) of dry pyridine, and 2 ml. of dry methanol is stirred for 3 hours at ambient temperature under nitrogen. The benzene is removed under reduced pressure, and additional benzene is added and removed three more times leaving a residue. The residue is taken up in benzene-pH6.6 aqueous buffer; the benzene layer is dried ($Na_2SO_4$), and evaporated to give 309 mg. of the above named product as a residue, pmr ($DCCl_3$) $\tau$ 8.43 (9H,s, t-butyl), 7.93 (3H, s, C-3 methyl), 6.63 (2H, q, J=19Hz, C-2), 610 (3H, s, $-OCH_3$), 5.10 (1H, d, J=5Hz, C-6), 4.83 (1H, s, C-7), 1.7–2.8 (5H, m, aromatics); ir ($CHCl_3$) 1775 ($\beta$-lactam), 1715 (ester C=O), and 1650 cm$^{-1}$.

EXAMPLE 8

7-[Methoxyphenylmethylene)amino]desacetoxycephalosporanic acid t-butyl ester

A mixture of 1 mmole of 7-aminodesacetoxycephalosporanic acid t-butyl ester, 1 mmole of trimethyl orthobenzoate, and 20 mg. of p-toluenesulfonic acid monohydrate in 50 ml. of dry benzene is refluxed under nitrogen for 4 hours. Approximately 10 ml. of benzene is gradually removed by distillation during the 4 hours. The reaction mixture is evaporated under reduced pressure to a residue that is taken up in benzene-water. The pH is adjusted with dilute aqueous sodium bicarbonate to 8, and the benzene layer is washed with the bicarbonate solution nd then with water. The benzene layer is washed with dilute hydrochloric acid solution at pH 2.5, then water, and finally dried ($Na_2SO_4$), and evaporated to give 353 mg. of the above named product as a residue. The pmr and ir spectra of this material is identical to that obtained for the product from Example 7.

EXAMPLE 9

7-[(Methoxyphenylmethylene)amino]cephalosporanic acid t-butyl ester

By following the procedure in Example 8 but substituting 7-aminocephalosporanic acid t-butyl ester for 7-aminodesacetoxy cephalosporanic acid t-butyl ester, the above named product is obtained as an amorphous residue. On addition of acetonepetroleum ether, the product is obtained as a crystalline compound, m.p. 130°–134° ; pmr ($DCCl_3$) $\tau$ 8.43 (9H,s,t-butyl), 7.92 (3H,s,O-acetyl), 6.53 (2H,q, J=19Hz, C-2), 5.07(2H,q, J=14Hz, C-3 methylene), 5.03(1H,d,J=5Hz, C-6), 4.77(1H, d, J=5Hz, C-7), 2.2–2.8 (5H,m, aromatics); ir($CHCl_3$) 1780 ($\beta$-lactam C=O), 1720–1740 (ester carbonyls) and 1650$^{cm1}$ (C=N).

EXAMPLE 10

7-[(Ethoxyphenylmethylene)amino]cephalosporanic acid benzhydryl ester

By following the procedure in Example 8 but substituting 7-aminocephalosporanic acid benzhydryl ester for 7-aminodesacetoxycephalosporanic acid t-butyl ester and triethyl orthobenzoate for trimethyl orthobenzoate, the above named product is obtained as an amorphous residue.

EXAMPLE 11

7-[(Methoxymethylene)amino]cephalosporanic acid t-butyl ester

By following the procedure of Example 9, but substituting trimethyl orthoformate for trimethyl orthobenzoate, the above named product is obtained as an amorphous residue.

EXAMPLE 12

7-[(1-Methoxy-2-phenylethylidene)amino]desacetoxycephalosporanic acid t-butyl ester By following the procedure of Example 7, but substituting the product of Example 3 for the imino chloride used in Example 7, the above named product is obtained as an amorphous residue.

EXAMPLE 13

7-[(1-Methoxy)ethylidene]amino]cephalosporanic acid t-butyl ester

By following the procedure of Example 9 but substituting trimethyl orthoacetate for trimethylorthobenzoate, the above named product is obtained as an amorphous residue.

EXAMPLE 14

7-[(1-Methoxypentylidene)amino]cephalosporanic acid t-butyl ester

By following the procedure of Example 9, but substituting trimethyl orthovalerate for trimethyl orthobenzoate, the above named product is obtained as an amorphous residue.

EXAMPLE 15

7-[[Methylthio methylene]amino]cephalosporanic acid t-butyl ester

By following the procedure of Example 9, but substituting trimethyl trithioorthoformate for trimethyl orthobenzoate, the above named product is obtained as an amorphous residue.

EXAMPLE 16

7-[[Ethylthio methylene]amino]cephalosporanic acid t-butyl ester

By following the procedure of Example 9 but substituting triethyl trithioorthoformate for trimethyl orthobenzoate, the above named product is obtained as an amorphous residue.

EXAMPLE 17

7-[[(Methylthio)phenylmethylene]amino]desacetoxycephalosporanic acid t-butyl ester By following the procedure of Example 8, but substituting trimethyl trithioorthobenzoate for trimethyl orthobenzoate, the above named product is obtained as an amorphous residue.

EXAMPLE 18

7-[[(Methylthio)phenylmethylene]amino]cephalosporanic acid benzhydryl ester

By following the procedure of Example 8, but substituting 7-aminocephalosporanic acid benzhydryl ester for 7-aminodesacetoxy cephalosporanic acid t-butyl ester and trimethyl trithioorthobenzoate for trimethyl orthobenzoate, the above named product is obtained as an amorphous residue.

EXAMPLE 19

7-(Chlorophenylmethylene)amino-7α-(methylthio)-desacetoxycephalosporanic acid t-butyl ester To a stirred solution of the product of Example 1 (786 mg., 2 mmoles) and methyl methanethiosulfonate (315 mg., 2.5 mmoles) in 30 ml. of dimethoxyethane at −70° C. under nitrogen is added potassium t-butoxide (224 g., 2 mmoles). The mixture is stirred at −70° C. for 30 minutes and poured into a mixture of aqueous pH 6.6 buffer-ice-chloroform. The chloroform extract is washed with saturated sodium chloride solution, dried ($Na_2SO_4$), and evaporated to give 631 mg. of the above named product as a residue, pmr ($DCCl_3$) τ 8.43 (9H,s, t-butyl), 7.85 (3H,s,C-3 methyl), 7.52 (3H,s,—$SCH_3$), 6.73 (2H,q, J=19Hz, C-2), 4.78 (1H,s,C-6), and 1.6–2.8 (5H,m,aromatics); ir($CHCl_3$) 1780 (β-lactam C=O), 1720 (ester C=O), and 1640 $cm^{-1}$ (c=N).

EXAMPLE 20

7-(Chlorophenylmethylene)amino-7α-(methylthio)-cephalosporanic acid t-butyl ester By following the procedure of Example 19, but substituting the product of Example 4 of the product of Example 1, the above named product is obtained as an amorphous residue.

EXAMPLE 21

7-(Bromophenylmethylene)amino-7α-(methylthio)-desacetoxycephalosporanic acid t-butyl ester By following the procedure of Example 19, but substituting the product of Example 2 for the product of Example 1, the above named product is obtained as an amorphous residue.

EXAMPLE 22

7-(Phenylacetamido)-7α-(methylthio)desacetoxycephalosporanic acid t-butyl ester

To a stirred solution of 7-[(1-chloro-2-phenylethylidene)amino]desacetoxycephalosporanic acid (1 mmole) and methyl methanethiosulfonate (1.25 mmole) in 8 ml. of dry dimethoxyethane at −70° under nitrogen is added potassium t-butoxide (1.5 mmoles). The mixture is stirred for 30 minutes at −70° and poured into pH 6.6 buffer-ice-chloroform. The chloroform extract is washed with saturated sodium chloride solution, dried ($Na_2SO_4$), and evaporated to a residue. The residue is hydrolyzed and purified by silica gel tlc, which yields 7-phenylacetamido-7α-(methylthio)desacetoxycephalosporanic acid t-butyl ester; pmr ($DCCl_3$) τ 8.50(9H,s,t-butyl), 7.92 (3H,s, C-3 methyl), 7.75 (3H,s,—$SCH_3$), 6.82 (2H, broad s, C-2), 6.36 (2H, broad s, $ArCH_2$—C=O), 5.09 (1H,s,C-6), 3.64 (1H,s,N—H), and 2.67 (5H,s,aromatics); ir ($CHCl_3$) 1775 (β-lactam C=O), 1712 (ester C=O), and 1675 $cm^{-1}$ (amide C=O).

EXAMPLE 23

7α-(Methylthio)-7-[(2-thienyl)acetamido]cephalosporanic acid trichloroethyl ester To a stirred mixture of the product of Example 5 (2 mmoles) and methyl methanethiosulfonate (2 mmoles) in 20 ml. of dimethoxyethane at −70° C. under nitrogen is added potassium t-butoxide (2 mmoles). The mixture is stirred at −70° for 45 minutes and poured into pH 6.6 buffer-ice-chloroform. The chloroform extract is washed with saturated sodium chloride solution, dried ($Na_2SO_4$), and evaporated to a residue. The residue is hydrolyzed and purified by chromatographing on silica to give the above named product as an amorphous residue.

EXAMPLE 24

7-(Cyanomethylthio)acetamido-7α-(methylthio)cephalosporanic acid benzhydryl ester By following the procedure in Example 23, but substituting the product of Example 6 for the imino chloride of Example 5, the above named product is obtained as an amorphous residue.

EXAMPLE 25

7-phenylacetamido-7α-(methylthio)cephalosporanic acid t-butyl ester

To a stirred solution of 7-[(1-chloro-2-phenylethylidene)amino]cephalosporanic acid t-butyl ester (1 mmole) in 6 ml. of dry dimethoxyethane at −70° under nitrogen is added potassium t-butoxide (1 mmole). When the potassium t-butoxide has disappeared, methylsulfenyl chloride (1 mmole) is added. The mixture is stirred for an additional 30 minutes and poured into ice-pH 6.6 buffer-chloroform. The chloroform extract is washed with saturated sodium chloride solution, dried ($Na_2SO_4$), and evaporated to a residue. Chromatography of the residue on silica gel yields 7-phenylacetamido-7α-(methylthio) cephalosporanic acid t-butyl ester as an amorphous residue.

EXAMPLE 26

7-(Benzamido)-7α-(ethylthio)aminodesacetoxycephalosporanic acid t-butyl ester By following the procedure of Example 25 but substituting the product of Example 1 for the imino chloride in Example 25 and ethylsulfenyl chloride for methylsulfenyl chloride, the above named product is obtained as an amorphous residue.

EXAMPLE 27

7-(Chlorophenylmethylene)amino-7α-(phenylthio)-cephalosporanic acid t-butyl ester By following the procedure of Example 25 but substituting the product of Example 4 for the imino chloride in Example 25 and phenylsulfenyl chloride for methylsulfenyl chloride, the above named product is obtained as an amorphous residue.

EXAMPLE 28

7-Benzamido-7α-(methylthio)desacetoxycephalosporanic acid t-butyl ester

A mixture of the product of Example 19 (1 mmole), 10 ml. of chloroform and 1 ml. of 1N hydrochloric acid is stirred at room temperature under nitrogen for 16 hours. The mixture is diluted with chloroform and water, and the chloroform layer is washed twice with water, dried, and evaporated to give the product 7-benzamido-7α-(methylthio)desacetoxycephalosporanic acid t-butyl ester as a residue, pmr ($DCCl_3$) τ 8.45(9H,s, t-butyl), 7.83(3H,s,C-3 methyl), 7.57(3H,s,—$SCH_3$), 6.67 (2H,broad s, C-2), 4.90(1H,s,C-6), 3.00(1H, broad s, N—H), 1.9–2.7 (5H,m,aromatics), ir($CHCl_3$) 1780(β-lactam C=O), 1720(ester C=O), and 1675 $cm^{-1}$ (amide C=O).

EXAMPLE 29

7-(Methoxyphenylmethylene)amino-7α-(methylthio)-desacetoxy cephalosporanic acid t-butyl ester A mixture of the product of Example 19 (2 mmoles) and pyridine (2 mmoles) in 15 ml. of anhydrous methanol is stirred for 3 hours at ambient temperature under nitrogen. The solvent is removed under reduced pressure, and benzene is added and removed under vacuum. The addition and removal of benzene is repeated two more times. The residue is taken up in benzene and water, and the pH is adjusted to 2.5. The benzene layer, after extraction, is washed twice with water, dried ($Na_2SO_4$) and evaporated to a residue. Chromatography of the residue on silica gel in the system benzene:ethyl acetate (19:1) yields the above named product as an amorphous residue, pmr($DCCl_3$) τ 8.45 (9H,s,t-butyl), 7.92(3H,s,C-3 methyl), 7.77 (3H,s,—$SCH_3$), 6.70 (2H,q,J=19Hz, C-2), 6.17(3H,s,$OCH_3$), 5.00 (1H,s,C-6), and 2.0–2.7(5H,m,aromatics); ir($CHCl_3$) 1780(β-lactam C=O), 1720 (ester C=O), and 1655 $cm^{-1}$ (c=N); mass spectrum molecular ion at m/e 434, base peak at m/e 178.

EXAMPLE 30

7-(Methoxyphenylmethylene)amino-7α-(methylthio)-cephalosporanic acid t-butyl ester By following the procedure of Example 29, but substituting the product of Example 20, the above named product is obtained as an amorphous residue.

EXAMPLE 31

7α-(Methylthio)-7-[(propoxyphenylmethylene)amino]-desacetoxycephalosporanic acid t-butyl ester By following the procedure of Example 29, but substituting n-propanol for methanol, the above named product is obtained as an amorphous residue.

EXAMPLE 32

7α-(Methylthio)-7-[[(methylthio)phenylmethylene]-amino]desacetoxycephalosporanic acid t-butyl ester By following the procedure for Example 29, but substituting a solution of methyl mercaptan (10 mmoles) in 10 ml. of dichloromethane for methanol, the above named product is obtained as an amorphous residue.

EXAMPLE 33

7α-(Methylthio)-7-[[(ethylthio)phenylmethylene)]-amino]cephalosporanic acid t-butyl ester By following the procedure of Example 29, but substituting a solution of ethyl mercaptan (10 mmoles) in 10 ml. of dichloromethane for methanol, and the product of Example 20 as starting material the above named product is obtained as an amorphous residue.

EXAMPLE 34

7-[[Chloro(4-nitrophenyl)methylene]amino]desacetoxycephalosporanic acid trichloroethyl ester By following the procedure of Example 1, but substituting 7-(4-nitrobenzamido)desacetoxycephalosporanic acid trichloroethyl ester for the 7-(benzamido)-desacetoxycephalosporanic acid t-butyl ester, the above named product is obtained as an amorphous residue.

EXAMPLE 35

7-[[Chloro(4-chlorophenyl)methylene]amino]cephalosporanic acid trichloroethyl ester By following the procedure of Example 1, but substituting 7-(4-chlorobenzamido)cephalosporanic acid trichloroethyl ester for 7-(benzamido)desacetoxycephalosporanic acid t-butyl ester, the above named product is obtained as an amorphous residue.

EXAMPLE 36

7-(Chlorophenylmethylene)amino-3-desacetoxy-3-[(2-methyl-1,3,4-thiadiazol-5-yl)thio]cephalosporanic acid benzhydryl ester By following the procedure of Example 1 but substituting 7-benzamido-3-desacetoxy-3-[(2-methyl-1,3,4-thiadiazol-5-yl)thio]cephalosporanic acid benzhydryl ester for 7-(benzamido)desacetoxycephalosporanic acid t-butyl ester, the above named product is obtained as an amorphous residue.

EXAMPLE 37

7-[[Bromo(4-chlorophenyl)methylene]amino]cephalosporanic acid p-methoxybenzyl ester By following the procedure of Example 2, but substituting 7-(4-chlorobenzamido)cephalosporanic acid p-methoxybenzyl ester for 7-(benzamido)desacetoxycephalosporanic acid t-butyl ester, the above named product is obtained as an amorphous residue.

EXAMPLE 38

7α-(Methylthio)-7-[[chloro-(4-nitrophenyl)methylene]amino]desacetoxycephalosporanic acid trichloroethyl ester By following the procedure of Example 19, but substituting the product of Example 34 for the product of Example 1, the above named product is obtained as an amorphous residue.

EXAMPLE 39

7α-(Methylthio)-7-[[chloro(4-chlorophenyl)methylene]amino]cephalosporanic acid trichloroethyl ester By following the procedure of Example 19, but substituting the product of Example 35 for the product of Example 1, the above named product is obtained as an amorphous residue.

EXAMPLE 40

7α-(Methylthio)-7-[(chlorophenylmethylene)amino]-3-desacetoxy-3-[(2-methyl-1,3,4-thiadiazol-5-yl)thio]cephalosporanic acid benzhydryl ester By following the procedure of Example 19, but substituting the product of Example 36 for the product of Example 1, the above named product is obtained as an amorphous residue.

EXAMPLE 41

7α-(Methylthio)-7-[[bromo(4-chlorophenyl)methylene]amino]cephalosporanic acid p-methoxybenzyl ester By following the procedure of Example 19, but substituting the product of Example 37 for the product of Example 1, the above named product is obtained as an amorphous residue.

EXAMPLE 42

7α-(Methylthio)-7-[[methoxy(4-nitrophenyl)methylene]amino]desacetoxycephalosporanic acid trichloroethyl ester By following the procedure of Example 29, but substituting the product of Example 38 for the product of Example 19, the above named product is obtained as an amorphous residue.

EXAMPLE 43

7α-(Methylthio)-7-[[methoxy(4-chlorophenyl)methylene]amino]cephalosporanic acid trichloroethyl ester By following the procedure of Example 29, but substituting the product of Example 39 for the product of Example 19, the above named product is obtained as an amorphous residue.

EXAMPLE 44

7α-(Methylthio)-7-(methoxyphenylmethylene)amino-3-desacetoxy-3-[(2-methyl-1,3,4-thiadiazol-5-yl)thio]cephalosporanic acid benzhydryl ester By following the procedure of Example 29, but substituting the product of Example 40 for the product of Example 19, the above named product is obtained as an amorphous residue.

EXAMPLE 45

7α-(Methylthio)-7-[[methoxy(4-chlorophenyl)methylene]amino]cephalosporanic acid p-methoxybenzyl ester By following the procedure of Example 29, but substituting the product of Example 41 for the product of Example 19, the above named product is obtained as an amorphous residue.

EXAMPLE 46

7α-(Methylthio)-7-[[methylthio(4-chlorophenyl)methylene]amino]cephalosporanic acid trichloroethyl ester By following the procedure of Example 29, but substituting the product of Example 39 for the product of Example 19, and methyl mercaptan (10 mmoles) in 10 ml. of dichloromethane for methanol, the above named product is obtained as an amorphous residue.

EXAMPLE 47

7α-(Methylthio)-7-[[methylthio(4-nitrophenyl)methylene]amino]desacetoxycephalosporanic acid trichloroethyl ester By following the procedure for Example 29, but substituting the product of Example 38 for the product of Example 19, and methyl mercaptan (10 mmoles) in 10 ml. of dichloromethane for methanol, the above named product is obtained as an amorphous residue.

EXAMPLE 48

7α-(Methylthio)-7-[(methylthio)phenylmethylene]amino-3-desacetoxy-3-[(2-methyl-1,3,4-thiadiazol-5-yl)thio]cephalosporanic acid benzhydryl ester By following the procedure of Example 29, but substituting the product of Example 40 for the product of Example 19, and methyl mercaptan (10 mmoles) in dichloromethane for methanol, the above product is obtained as an amorphous residue.

EXAMPLE 49

7α-(Methylthio)-7-[methylthio(4-chlorophenyl)methylene]aminocephalosporanic acid p-methoxybenzyl ester By following the procedure of Example 29, but substituting the product of Example 41 for the product of Example 19, and methyl mercaptan (10 mmoles) in dichloromethane for methanol, the above named product is obtained as an amorphous residue.

EXAMPLE 50

7α-(Methylthio)-7-[(methoxyphenylmethylene)amino]-desacetoxycephalosporanic acid t-butyl ester To a stirred mixture of 7-[(methoxyphenylmethylene)amino]desacetoxycephalosporanic acid t-butyl ester (1 mmole) and methyl methanethiol sulfonate (1.25 mmole) in dimethoxyethane at $-70°$ C. under nitrogen is added potassium t-butoxide (1 mmole) mixture is stirred at $-70°$ C. for 30 minutes and poured into ice-pH6.6 buffer-chloroform. The chloroform extract is washed with saturated sodium chloride solution, dried ($Na_2SO_4$), and evaporated to a residue. The residue is purified by chromatography on silica gel to give the above named product as an amorphous residue.

EXAMPLE 51

7α-(Methylthio)-7-[(methoxyphenylmethylene)amino]-cephalosporanic acid t-butyl ester By following the procedure of Example 50 but substituting the product of Example 9 for the product of Example 8, the above named product is obtained as an amorphous residue. It has: pmr ($DCCl_3$) τ 8.43 (9H,s,t-butyl), 7.90 (3H,s,O-acetyl), 7.75 (3H,s,$SCH_3$), 6.75, 6.38 (2H,q,J=19H,z,C-2), 6.13 (3H,s,$OCH_3$), 5.23, 4.87 (2H,q,J=13Hz,C-3 methylene), 5.00 (1H,s,C-6), 2.0–2.7 (5H,m,aromatics); ir ($CHCl_3$) 1785 (B-lactam C=O), 1730 (ester C=Os), and 1645 $cm^{-1}$ (C=N).

EXAMPLE 52

7α-(Methylthio)-7-[(ethoxyphenylmethylene)amino]-cephalosporanic acid benzhydryl ester By following the procedure of Example 50, but substituting the product of Example 10 for the product of Example 8, the above named product is obtained as an amorphous residue.

EXAMPLE 53

7α-(Methylthio)-7-[(methoxymethylene)amino]cephalosporanic acid t-butyl ester

By following the procedure of Example 50, but substituting the product of Example 11 for the product of Example 8, the above named product is obtained as an amorphous residue.

EXAMPLE 54

7α-(Methylthio)-7-[(1-methoxy-2-phenylethylidene)amino]desacetoxycephalosporanic acid t-butyl ester By following the procedure of Example 50, but substituting the product of Example 12 for the product of Example 8, the above named product is obtained as an amorphous residue.

EXAMPLE 55

7α-(Methylthio)-7-[(1-methoxyethylidene)amino]cephalosporanic acid t-butyl ester By following the procedure of Example 50, but substituting the product of Example 13 for the product of Example 8, the above neamed product is obtained as an amorphous residue.

EXAMPLE 56

7α-(Methylthio)-7-[(1-methoxypentylidene)amino]-cephalosporanic acid t-butyl ester By following the procedure of Example 50, but substituting the product of Example 14 for the product of Example 8, the above named product is obtained as an amorphous residue.

EXAMPLE 57

7α-(Methylthio)-7-[[methylthio methylene]amino]cephalosporanic acid t-butyl ester By following the procedure of Example 50, but substituting the product of Example 15 for the product of Example 8, the above named product is obtained as an amorphous residue.

EXAMPLE 58

7α-(Methylthio)-7-[[ethylthio methylene]amino]cephalosporanic acid t-butyl ester By following the procedure of Example 50, but substituting the product of Example 16, the above named product is obtained as an amorphous residue.

EXAMPLE 59

7α-(Methylthio)-7-[[methylthio phenylmethylene]amino]desacetoxycephalosporanic acid t-butyl ester By following the procedure of Example 50, but substituting the product of Example 17 for the product of Example 8, the above named product is obtained as an amorphous residue.

EXAMPLE 60

7α-(Methylthio)-7-[[(methylthio)phenylmethylene]-amino]cephalosporanic acid benzhydryl ester By following the procedure of Example 50, but substituting the product of Example 18 for the product of Example 8, the above named product is obtained as an amorphous residue.

EXAMPLE 61

7α-(Methylthio)-7-[(methoxyphenylmethylene)amino]-cephalosporanic acid t-butyl ester To a stirred solution of triphenylmethane (1 mmole) in 10 ml. of dry tetrahydrofuran under nitrogen at ambient temperature is added n-butyl lithium (1.25 mmole) in n-hexane. The red solution is stirred for 15 minutes and then cooled to $-70°$ C. A solution of 7-[(methoxyphenylmethylene)amino]cephalosporanic acid t-butyl ester (1 mmole) in 3 ml. of tetrahydrofuran is quickly added, and after stirring for 1 minute, a solution of methyl methanethiol sulfonate (1.25 mmole) in 2 ml. of tetrahydrofuran is added. The mixture is stirred at $-60°$ to $-50°$ C. for 30 minutes, and poured into ice-pH 6.6 buffer- chloroform. The chloroform extract is washed with saturated sodium chloride, dried ($Na_2SO_4$), and evaporated to residue. The residue is purified by chromatography on silica gel to give the above named product as an amorphous material.

EXAMPLE 62

7α-(Methylthio)-7-[(methoxyphenylmethylene)amino]cephalosporanic acid t-butyl ester To a stirred solution of lithium cyclohexylisopropylamide (1 mmole) in 6 ml. of dry dimethylformamide at −60° C. under nitrogen is added 1 mmole of 7-[(methoxyphenylmethylene)amino]cephalosporanic acid t-butyl ester. The mixture is stirred at −60° C for 2 minutes, and then methyl methanethiol sulfonate (1.25 mmole) is added. The mixture is stirred at −60° for 45 minutes and poured into ice-pH 6.6 buffer-chloroform. The mixture is extracted repeatedly with chloroform, and the chloroform extract is washed four times with water, dried ($Na_2SO_4$), and evaporated under reduced pressure to a residue. The residue is chromatographed on silica gel to give the above named product as an amorphous material.

EXAMPLE 63

7α-(Methylthio)-7-(phenylacetamido)desacetoxycephalosporanic acid t-butyl ester

Method A

To a mixture of the 7α-(methylthio)-7-[(methoxyphenylmethylene)amino]desacetoxycephalosporanic acid t-butyl ester product of Example 50 (1 mmole) and phenylacetyl chloride (1 mmole) in 10 ml. of dichloromethane is added 1 ml. of 1N hydrochloric acid. The mixture is stirred under nitrogen at ambient temperature, the progress of reaction is followed by silica gel thin layer chromatography (QIF plates) in the system benzene:ethylacetate (19:1), using short-wavelength UV light for visualization. After 21 hours, the mixture is diluted with dichloromethane and water. The aqueous layer is discarded, and the dichloromethane is layered with water. The pH is adjusted to 8.0 and the dichloromethane is removed, washed with water, dried ($Na_2SO_4$), and evaporated under reduced pressure to a residue. The residue is chromatographed on silica gel to give 7α-(methylthio)-7-(phenylacetamido)desacetoxycephalosporanic acid t-butyl ester as an amorphous residue.

Method B

By following the foregoing procedure of Method A, but substituting pyridine (1 mmole) and water (5 mmoles) for the 1 ml. of 1N hydrochloric acid, 7α-(methylthio)-7-(phenylacetamido)desacetoxycephalosporanic t-butyl ester is obtained as an amorphous residue.

By following the procedure of Example 63, but using the indicated material of formula III in Table I instead of 7α-(methylthio)-7-[(methoxyphenylmethylene)amino]desacetoxycephalosporanic acid t-butyl ester and the acylating agent shown in the Table I instead of phenylacetyl chloride, the 7-acylated-7-thio-substituted product shown in Table I is obtained as an amorphous residue by the procedure of Example 63 indicated in the last column:

TABLE I

| Ex. | Acylating Agent | R² | R³ | R⁴ | X | R | R¹ | Method |
|---|---|---|---|---|---|---|---|---|
| 64 | ClC(O)CH₂-C₆H₅ | C₆H₅ | CH₃O— | CH₃— | CH₃C(O)O— | t-butyl | C₆H₅-CH₂— | A |
| 65 | ClC(O)CH₂-S-CH₂-CN | C₆H₅ | CH₃O— | CH₃— | CH₃C(O)O— | t-butyl | NC-CH₂-S-CH₂— | A |
| 66 | ClC(O)CH(C₆H₅)(phthalimido) | C₆H₅ | CH₃O— | CH₃— | CH₃C(O)O— | t-butyl | C₆H₅-CH(phthalimido)— | A |
| 67 | PhCH(NHCO₂CH₂C₆H₅)C(O)OC(O)OC₂H₅ | C₆H₅ | CH₃O— | CH₃— | H | 4-CH₃O-C₆H₄-CH₂— | C₆H₅-CH(NH₂)— | A |

TABLE I-continued (III) [structure shown]
(IV) [structure shown]

| Ex. | Acylating Agent | R² | R³ | R⁴ | X | R | R¹ | Method |
|---|---|---|---|---|---|---|---|---|
| 68 | thiophene-CH₂-C(O)-Cl | 4-O₂N-C₆H₄- | CH₃O— | CH₃— | CH₃-C(O)-O— | Cl₃C-CH₂- | thiophene-CH₂- | B |
| 69 | C₆H₅-S-CH₂-C(O)-Cl | 4-Cl-C₆H₄- | CH₃O— | CH₃CH₂— | H | (C₆H₅)₂CH- | C₆H₅-S-CH₂- | B |
| 70 | NC-CH₂CH₂S-CH₂-C(O)-Cl | C₆H₅- | CH₃O | CH₃ | CH₃-C(O)-O | t-butyl | NC-CH₂CH₂SCH₂- | A |
| 71 | Cl-CH₂-C(O)-Cl | 4-O₂N-C₆H₄- | CH₃O | CH₃ | CH₃-C(=N-N=)-S— | t-butyl | Cl-CH₂- | A |
| 72 | C₆H₅-CH₂-C(O)-Cl | CH₃— | CH₃O | CH₃ | CH₃-C(O)-O— | (C₆H₅)₂CH- | C₆H₅-CH₂- | B |
| 73 | thiophene-CH₂-C(O)-Cl | CH₃CH₂-CH₂— | CH₃O | CH₃ | CH₃-C(O)-O— | t-butyl | thiophene-CH₂- | A |

TABLE I-continued (III) / (IV) structures shown with R², R³, R⁴ substituents and CH₂X, OR, etc.

| Ex. | Acylating Agent | R² | R³ | R⁴ | X | R | R¹ | Method |
|---|---|---|---|---|---|---|---|---|
| 74 | (thiophene)-CH₂-CH(NH-C(=O)-O-CH₂-phenyl)-C(=O)-O-C(=O)-O-i-butyl | H | CH₃O | CH₃ | CH₃C(=O)-O- | t-butyl | (thiophene)-CH(NH₂)- | A |
| 75 | (thiophene)-CH₂-C(=O)-Cl | phenyl | CH₃S- | CH₃- | H | Cl₃CCH₂ | (thiophene)-CH₂- | B |
| 76 | NC-CH₂-S-CH₂-C(=O)-Cl | phenyl | CH₃S- | CH₃- | CH₃C(=O)-O- | t-butyl | NC-CH₂-S-CH₂- | A |
| 77 | phenyl-CH₂-C(=O)-Cl | phenyl | CH₃CH₂S- | CH₃- | CH₃C(=O)-O- | t-butyl | phenyl-CH₂- | A |
| 78 | 4-Cl-phenyl-CH₂-C(=O)-Cl | 4-Cl-phenyl | CH₃S | phenyl | CH₃C(=O)-O- | Cl₃CCH₂ | phenyl-CH₂- | A |
| 79 | 4-O₂N-phenyl-O-CH₂-C(=O)-Cl | 4-O₂N-phenyl | CH₃S | CH₃- | H | Cl₃CCH₂ | phenyl-O-CH₂- | B |

TABLE I-continued

Structure (III): R²—C(R³)=N—C(R⁴)(S—)—C(=O)—N—CH—CH₂—S—C(=CH₂X)—C(=O)OR

Structure (IV): R¹—C(=O)—NH—C(R⁴)(S—)—C(=O)—N—CH—CH₂—S—C(=CH₂X)—C(=O)OR

| Ex. | Acylating Agent | R² | R³ | R⁴ | X | R | R¹ | Method |
|---|---|---|---|---|---|---|---|---|
| 80 | 2-thienyl-CH₂-C(=O)-Cl | phenyl | CH₃S | CH₃ | CH₃-C(=N-N)-S- (thiadiazolyl-S) | t-butyl | 2-thienyl-CH₂- | B |
| 81 | C₆H₅-CH(OCH₂C₆H₅)-C(=O)-Cl | 4-O₂N-C₆H₄- | CH₃CH₂S- | CH₃ | CH₃O | t-butyl | (C₆H₅)₂CH-OCH₂- | A |
| 82 | CH₃-CH₂-S-CH₂-C(=O)-Cl | 4-O₂N-C₆H₄- | CH₃S | CH₃CH₂ | H | Cl₃CCH₂- | CH₃CH₂S-CH₂- | A |
| 83 | 2-thienyl-CH(NH-C(=O)-O-C(=O)-OC₂H₅)-C(=O)-OCH₂C₆H₅ | CH₃CH₂-CH₂- | CH₃S | CH₃ | H | t-butyl | 2-thienyl-CH(NH₂)- | A |
| 84 | Cl-CH₂-C(=O)-Cl | H— | CH₃S | CH₃ | CH₃-C(=O)-O- | t-butyl | Cl-CH₂- | A |

TABLE I-continued
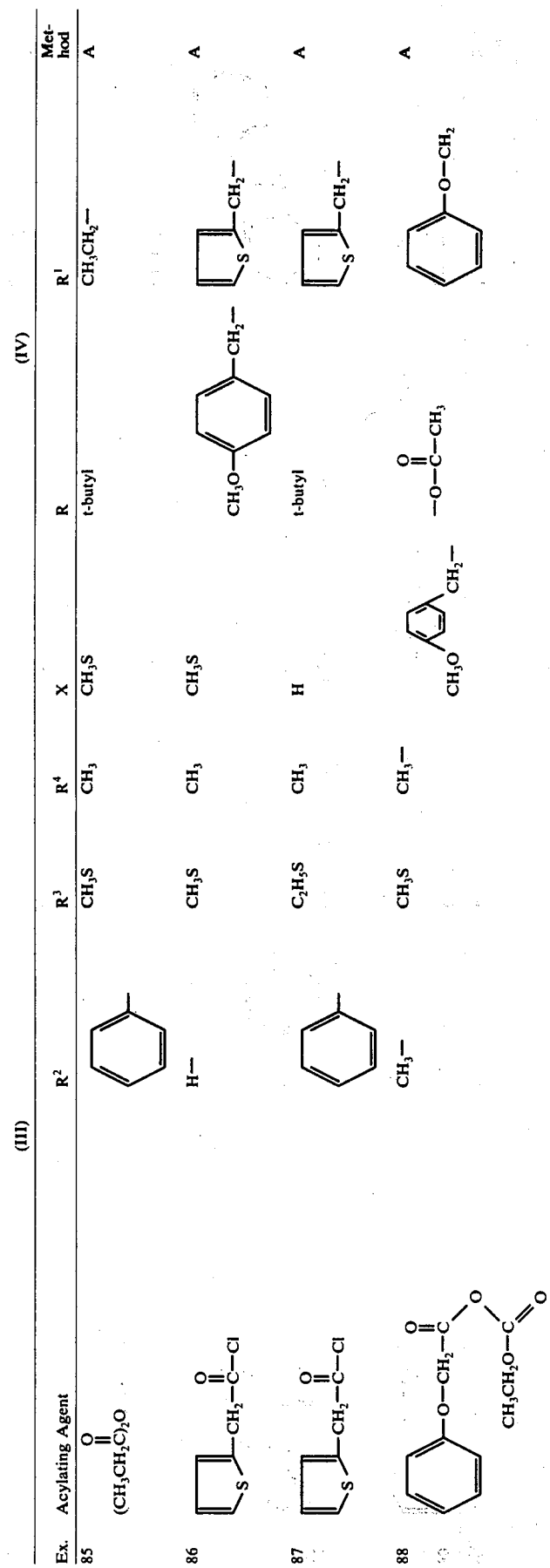
| Ex. | Acylating Agent | $R^2$ | $R^3$ | $R^4$ | X | R | $R^1$ | Method |
|---|---|---|---|---|---|---|---|---|
| 85 | $(CH_3CH_2C)_2O$ | phenyl | $CH_3S$ | $CH_3$ | $CH_3S$ | t-butyl | $CH_3CH_2-$ | A |
| 86 |  | H— | $CH_3S$ | $CH_3$ | $CH_3S$ | 4-$CH_3O$-benzyl | 2-thienylmethyl | A |
| 87 | (thienylmethyl-COCl) | phenyl | $C_2H_5S$ | $CH_3$ | H | t-butyl | 2-thienylmethyl | A |
| 88 | (PhOCH$_2$-O-CO-O-CO-OCH$_2$CH$_3$) | $CH_3-$ | $CH_3S$ | $CH_3-$ | 3-$CH_3O$-benzyl | $-O-C(=O)-CH_3$ | phenoxymethyl | A |

What is claimed is:
1. A compound of the formula

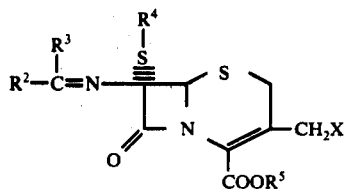

wherein $R^2$ is lower alkyl, lower alkoxy-lower alkyl, cyano-lower alkyl, cyanomethylthio-lower alkyl, phenyl-lower alkyl, phenoxy-lower alkyl, thienyl-lower alkyl, phenyl or phenyl substituted with halo, lower alkyl, nitro or carbo-lower alkoxy, $R^3$ is chloro, bromo, lower alkoxy, lower alkylthio or phenoxy, $R^4$ is lower alkyl, phenyl, benzyl or phenyl or benzyl substituted with nitro, halo, lower alkyl or carbo-lower alkoxy, $R^5$ is t-butyl, nitrobenzyl, methoxybenzyl, trichloroethyl, benzhydryl, trimethylsilyl, acetoxymethyl or pivaloyloxymethyl and X is hydrogen or lower alkanoyloxy.

2. A compound as in claim 1 wherein $R^3$ is chloro.
3. A compound as in claim 1 wherein $R^3$ is chloro, $R^5$ is t-butyl and X is hydrogen.
4. A compound as in claim 1 wherein $R^3$ is chloro, $R^5$ is t-butyl and X is acetoxy.
5. A compound as in claim 1 wherein $R^3$ is methylthio, $R^5$ is t-butyl and X is hydrogen.
6. A compound as in claim 1 wherein $R^3$ is methoxy, $R^5$ is t-butyl and X is acetoxy.
7. A compound as in claim 1 wherein $R^4$ is methyl.
8. A compound as in claim 3 wherein $R^2$ is phenyl and $R^4$ is methyl.
9. A compound as in claim 4 wherein $R^2$ is phenyl and $R^4$ is methyl.